(12) United States Patent
Isaacson et al.

(10) Patent No.: US 10,946,176 B2
(45) Date of Patent: Mar. 16, 2021

(54) INTRAVENOUS CATHETER ASSEMBLY WITH SAFETY CLIP

(71) Applicant: Becton, Dickinson and Company, Franklin Lakes, NJ (US)

(72) Inventors: S Ray Isaacson, Layton, UT (US); Bart D Peterson, Farmington, UT (US); Austin Jason McKinnon, Herriman, UT (US); Joseph Spataro, Sandy, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 303 days.

(21) Appl. No.: 15/481,166

(22) Filed: Apr. 6, 2017

(65) Prior Publication Data

US 2018/0289932 A1 Oct. 11, 2018

(51) Int. Cl.
*A61M 25/06* (2006.01)
*A61M 5/32* (2006.01)

(52) U.S. Cl.
CPC ...... *A61M 25/0618* (2013.01); *A61M 5/3273* (2013.01); *A61M 25/0606* (2013.01); *A61M 25/0631* (2013.01); *A61M 25/0693* (2013.01)

(58) Field of Classification Search
CPC .......... A61M 25/0612; A61M 25/0618; A61M 5/3273; A61M 25/0606; A61M 25/0631
See application file for complete search history.

(56) References Cited

U.S. PATENT DOCUMENTS

| | | | |
|---|---|---|---|
| 5,458,658 A | 10/1995 | Sircom | |
| 6,117,108 A | 9/2000 | Woehr et al. | |
| 6,186,984 B1 | 2/2001 | Fukutomi | |
| 6,203,527 B1* | 3/2001 | Zadini | A61M 5/3273 604/110 |
| 6,280,419 B1 | 8/2001 | Vojtasek | |
| 6,287,278 B1 | 9/2001 | Woehr et al. | |
| 6,652,490 B2 | 11/2003 | Howell | |
| 7,654,988 B2 | 2/2010 | Moulton et al. | |

(Continued)

FOREIGN PATENT DOCUMENTS

| | | |
|---|---|---|
| CN | 102725013 | 10/2012 |
| DE | 20315872 | 2/2004 |

(Continued)

*Primary Examiner* — Nathan R Price
*Assistant Examiner* — Weng Lee
(74) *Attorney, Agent, or Firm* — Kirton & McConkie; Craig Metcalf; Kevin Stinger

(57) ABSTRACT

A catheter assembly may include a catheter, catheter adapter, needle, needle guard, and housing. The housing may be coupled to the needle guard and disposed within a lumen of the catheter adapter. The needle guard may include first and second resilient arms, which may include first and second curved portions, respectively. When the needle is in a ready position, the first and second curved portions may be urged by a shaft of the needle into retaining contact with an inner wall of the catheter adapter. When the needle is in the retracted position, the shaft may no longer bias the first and second resilient arms outwardly such that the retaining contact between the first and second curved portions and the catheter adapter is released, and the housing and the needle guard enclose a distal tip of the needle.

20 Claims, 13 Drawing Sheets

(56) References Cited

U.S. PATENT DOCUMENTS

| | | |
|---|---|---|
| 7,713,243 B2 | 5/2010 | Hillman |
| 8,038,647 B2 | 10/2011 | Harding et al. |
| 8,398,597 B2 | 3/2013 | Brimhall |
| 8,858,503 B2 | 10/2014 | Burkholz et al. |
| 8,936,575 B2 | 1/2015 | Moulton |
| 2004/0049155 A1 | 3/2004 | Schramm |
| 2004/0092889 A1 | 5/2004 | Ferguson et al. |
| 2004/0236288 A1 | 11/2004 | Howell et al. |
| 2007/0073221 A1 | 3/2007 | Bialecki et al. |
| 2007/0270754 A1 | 11/2007 | Soderholm et al. |
| 2009/0281499 A1* | 11/2009 | Harding ............ A61M 25/0618 604/164.08 |
| 2012/0046620 A1* | 2/2012 | Woehr ............ A61M 25/0097 604/263 |
| 2013/0204207 A1* | 8/2013 | Kuracina ......... A61B 5/150633 604/263 |
| 2014/0025009 A1* | 1/2014 | Erskine ............ A61B 17/3494 604/164.08 |
| 2017/0049998 A1 | 2/2017 | Melsungen |

FOREIGN PATENT DOCUMENTS

| | | |
|---|---|---|
| EP | 0554841 | 8/1993 |
| EP | 1306097 | 5/2003 |
| EP | 2735331 | 5/2014 |
| FR | 2867083 | 9/2005 |
| GB | 2292525 | 2/1996 |
| WO | 98/53873 | 12/1998 |
| WO | 01/23029 | 4/2001 |
| WO | 02/096494 | 12/2002 |
| WO | 2004/091687 | 10/2004 |
| WO | 2005/079891 | 9/2005 |
| WO | 2006/062983 | 6/2006 |
| WO | 2008/021132 | 2/2008 |
| WO | 2013/124765 | 8/2013 |

* cited by examiner

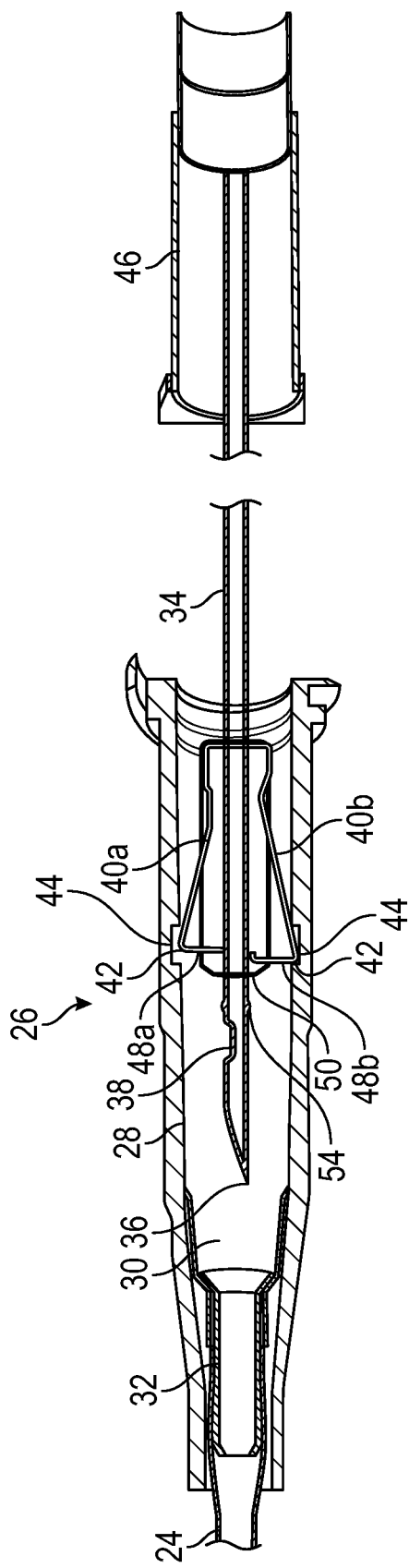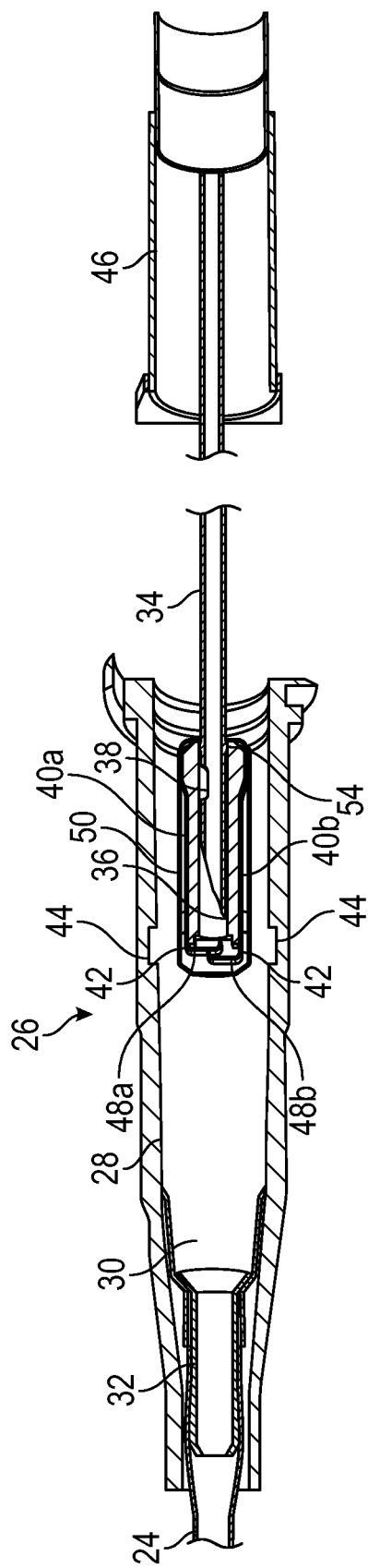

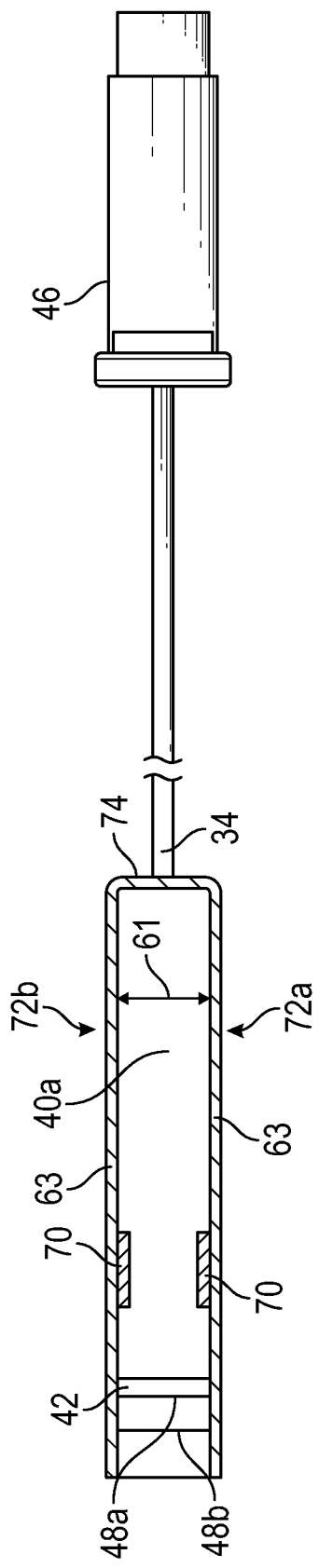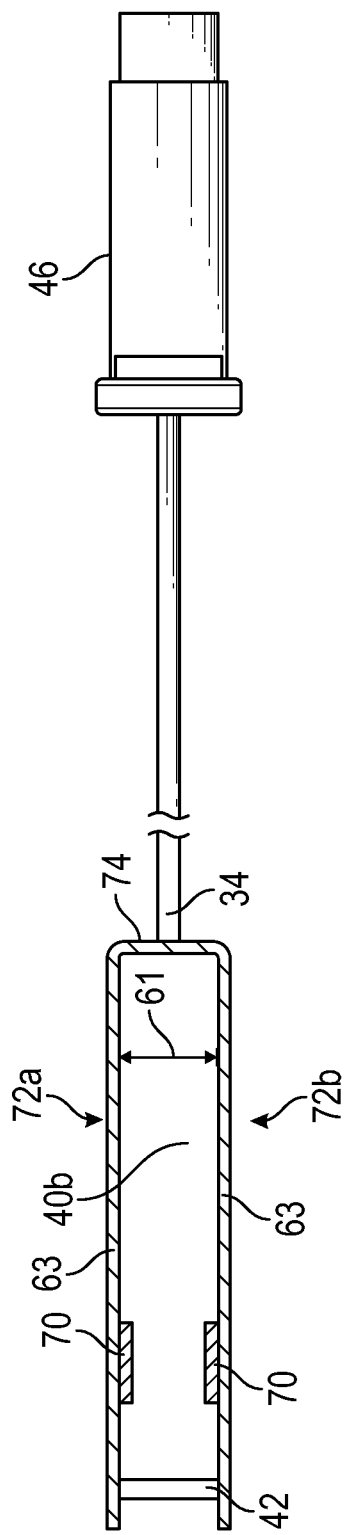
FIG. 5A
FIG. 5B

INTRAVENOUS CATHETER ASSEMBLY WITH SAFETY CLIP

BACKGROUND OF THE INVENTION

Intravenous (IV) catheter assemblies are among the various types of vascular access devices. Over-the-needle peripheral IV catheters are a common IV catheter configuration. As its name implies, an over-the-needle catheter may be mounted over an introducer needle having a sharp distal tip. The needle may be a hypodermic needle coupled to a needle assembly to help guide the needle and to facilitate its cooperation with the catheter. At least the inner surface of the distal portion of the catheter tightly may engage an outer surface of the needle to prevent peel back of the catheter and, thereby, facilitate insertion of the catheter into the blood vessel. The catheter and the needle may be assembled so that the distal tip of the needle extends beyond the distal tip of the catheter. Moreover, the catheter and the needle may be assembled so that, during insertion, the bevel of the needle faces up, away from skin of a patient. The catheter and needle may be inserted at a shallow angle through the skin into a blood vessel.

In order to verify proper placement of the needle and/or catheter in the blood vessel, the user may confirm that there is "flashback" of blood into a flashback chamber associated with the needle assembly. Flashback generally entails the appearance of a small amount of blood, which is visible within the needle assembly or between the needle and the catheter. Once proper placement of the distal tip of the catheter into the blood vessel is confirmed, the user may apply pressure to the blood vessel by pressing down on the skin over the blood vessel, distal to the needle and the catheter. This finger pressure may momentarily occlude the vessel, reducing further blood flow through the needle and the catheter.

The user may then withdraw the needle from the catheter, and in some instances, the needle assembly may be separated from catheter portions of the catheter assembly. The separation of the needle assembly from catheter portions of the catheter assembly presents numerous potential hazards to the users and others in the area. There may be a risk of accidental needle sticks if the distal tip is not secured properly. Additionally, because the needle has been in contact with blood in vasculature of the patient, blood may be present on an exterior of the needle as well as inside a lumen of the needle. As the needle is withdrawn from the catheter, there is a risk that the blood will drip from the distal tip or come into contact with other surfaces to expose people and equipment to blood.

Additionally, it has been observed that withdrawing the needle from a catheter assembly may impart energy to parts of the needle assembly. For instance, during withdrawal of the introducer, bending forces can be applied (either unintentionally or intentionally) to the needle. The bending forces on the needle may cause blood to splatter or spray from the needle when the needle vibrates and shakes as it becomes free from the catheter assembly and releases stored energy. Accordingly, there is a need in the art for devices, systems, and methods that provide catheter assemblies with increased needle safety.

BRIEF SUMMARY OF THE INVENTION

The present disclosure relates generally to an IV catheter assembly and associated devices, systems, and methods. In some embodiments, the catheter assembly may be used for infusion and/or blood collection. In some embodiments, the catheter assembly may include a catheter, which may include a proximal end and a distal end. In some embodiments, the catheter assembly may include a catheter adapter, which may include an inner wall forming a lumen. In some embodiments, the proximal end of the catheter may be coupled with the catheter adapter.

In some embodiments, the catheter assembly may include a needle, which may include one or more of the following: an elongated shaft, a sharp distal tip, and a notch. In some embodiments, the notch may improve first stick success and allow observation of blood flashback. In some embodiments, the needle may be disposed within the catheter when the needle is in a ready position. In some embodiments, the needle may be movable between the ready position in which the distal tip is outside of the catheter adapter and a retracted position in which the distal tip is disposed within the lumen of the catheter adapter.

In some embodiments, the catheter assembly may include a needle guard, which may be unitary or integrally formed. In some embodiments, the needle guard may include a proximal end wall. In some embodiments, the proximal end wall may include an opening for receiving the needle there through. In some embodiments, the catheter assembly may include one or more resilient portions, which may be coupled with the proximal end wall. In some embodiments, each of the resilient portions may be urged by the elongated shaft into retaining contact with the inner wall of the catheter adapter when the needle is in the ready position and/or during movement of the needle between the ready position and the retracted position.

In some embodiments, when the needle is in the retracted position, the elongated shaft may no longer bias each of the resilient portions outwardly such that the retaining contact between each of the resilient portions and the catheter adapter are released. In these embodiments, the housing and the needle guard may be removable from the catheter adapter when the needle is in the retracted position. In some embodiments, the inner wall of the catheter adapter may include one or more retaining means, such as, for example, a groove. In some embodiments, a particular retaining means may receive a particular resilient portion when the needle is in the ready position and the particular resilient portion and the catheter adapter are in retaining contact. For example, the particular retaining means may receive a curved portion of the particular resilient portion when the needle is in the ready position and the particular resilient portion and the catheter adapter are in retaining contact.

In some embodiments, the catheter assembly may include one or more distal walls, which may each extend from the resilient portions. In some embodiments, each of the distal walls may include a lip, which may engage the elongated shaft of the needle when the needle is in the ready position. In some embodiments, each of the distal walls may be movable within the lumen of the catheter hub to blocking positions distal of the distal tip. In some embodiments, each of the distal walls may be in their respective blocking positions when the needle is in the retracted position. In some embodiments, the distal walls may contact and/or overlap one another and form a distal barrier to the needle when the distal walls are in their respective blocking positions.

In some embodiments, the catheter assembly may include a housing, which may be coupled to the needle guard and/or disposed within the lumen of the catheter adapter. In some embodiments, the housing and the needle guard may enclose the distal tip and/or the notch when the needle is in the retracted position. In some embodiments, the housing may include multiple shield elements, which may be spaced apart. For example, the housing may include a first shield element and a second shield element opposite the first shield element. In some embodiments, the first and second shield elements may be spaced apart by a gap. In some embodiments, one or more particular resilient portions may be urged outwardly by the elongated shaft through the gap when the needle is in the ready position.

In some embodiments, the housing may include one or more snap features configured to secure the needle guard within the housing when the needle is in the retracted position. In some embodiments, an inner surface and/or an inner edge of the first shield element may include one or more snap features. Additionally, in some embodiments, the inner surface and/or an inner edge of the second shield element may include one or more snap features. In some embodiments, the snap features may contact an outer surface of a particular resilient portion of the needle guard when the needle is in the retracted position. In some embodiments, the first snap feature may extend more inwardly than the second snap feature such that the particular resilient portion passes the second snap feature before the first snap feature when the needle moves from the ready position to the retracted position.

In some embodiments, an inner surface of the housing may include one or more distal features and/or one or more proximal features. In some embodiments, each of the distal features may be configured to contact a proximal surface of a particular distal wall of the needle guard to prevent the needle guard from sliding proximally with respect to the housing. In some embodiments, each of the proximal features may be configured to contact a distal surface of the proximal end wall to prevent the needle guard from sliding distally with respect to the housing. In some embodiments, the inner surface of the housing may include or correspond to an inner surface of one or more particular shield elements.

In some embodiments, the resilient portions may include elongated resilient arms. In particular, in some embodiments, the resilient portions may include a first and second resilient arm. In some embodiments, the first and second resilient arms may include first and second curved portions, respectively. In some embodiments, the first and second curved portions may be urged by the elongated shaft into retaining contact with the inner wall of the catheter adapter when the needle is in the ready position and/or during movement of the needle between the ready position and the retracted position. In some embodiments, when the needle is in the retracted position, the elongated shaft may no longer exert a force on the first and second resilient arms such that the retaining contact between the first and second curved portions and the catheter adapter is released. In some embodiments, the needle guard may include first and second distal walls, which may contact and/or overlap one another and form a distal barrier to the needle when the needle is in the retracted position. In some embodiments, the first and second resilient arms may extend between the first and second distal walls, respectively, and the proximal end wall.

In some embodiments, when the needle is in the ready position, the first resilient arm may be entirely disposed on a first side of the needle and the second resilient arm may be entirely disposed on a second side of the needle opposite the first side of the needle. In some embodiments, the first distal wall and the second distal wall may include first and second lips, respectively, which may engage the elongated shaft of the needle when the needle is in the ready position.

BRIEF DESCRIPTION OF THE SEVERAL VIEWS OF THE FIGURES

In order that the manner in which the above-recited and other features and advantages of the invention will be readily understood, a more particular description of the cannula capture mechanism briefly described above will be rendered by reference to specific embodiments thereof, which are illustrated in the appended Figures. Understanding that these Figures depict only typical embodiments and are not, therefore, to be considered to be limiting of its scope, the invention will be described and explained with additional specificity and detail through the use of the accompanying Figures in which:

FIG. 2B is a cross-sectional view of the catheter assembly of FIG. 2A, illustrating the needle between the ready position and a retracted position, according to some embodiments;

FIG. 2C is a cross-sectional view of the catheter assembly of FIG. 2A, illustrating the needle in the retracted position, according to some embodiments;

FIG. 5A is a top view of the needle assembly of FIG. 3A, illustrating the needle in the retracted position, according to some embodiments;

FIG. 5B is a bottom view of the needle assembly of FIG. 3A, illustrating the needle in the retracted position, according to some embodiments;

DETAILED DESCRIPTION OF THE INVENTION

The presently preferred embodiments of the described invention will be best understood by reference to FIGS. 1-6, wherein like parts are designated by like numerals throughout. It will be readily understood that the components of the present invention, as generally described and illustrated in FIGS. 1-6 in the present disclosure, could be arranged and designed in a wide variety of different configurations. Thus, the following more detailed description of the embodiments of the catheter assembly, and associated devices, systems, and methods, is not intended to limit the scope of the invention, as claimed, but is merely representative of some embodiments of the invention.

Figure 1A:
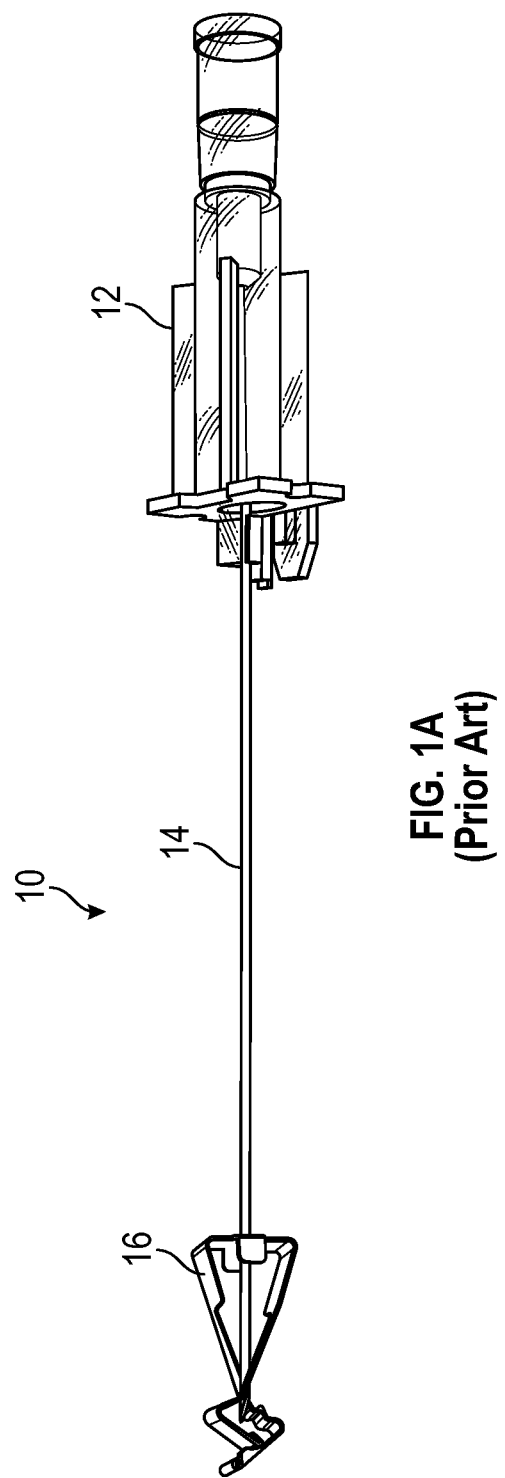
FIG. 1A is an upper perspective view of a prior art needle assembly.
Figure 1B:
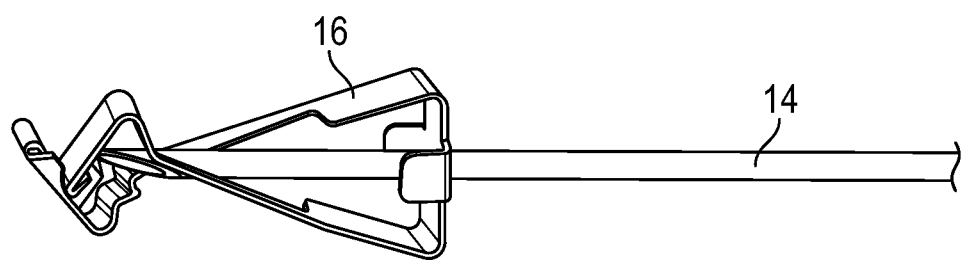
FIG. 1B is an enlarged upper perspective view of a portion of the needle assembly of FIG. 1A.

FIG. 1A illustrates a needle assembly 10 commonly used in the medical field. The needle assembly 10 may include a needle hub 12, a needle 14 extending distally from the needle hub, and a spring clip 16. The spring clip 16 is enlarged in FIG. 1B. The needle assembly 10 may be part of an IV catheter assembly (not illustrated in FIGS. 1A-1B) and may provide several functions. For example, when a needle 14 of the needle assembly 10 is in a ready position for insertion into a vein of a patient, flexible arms of the spring clip 16 may be urged outward and may interfere with a retention feature on an inner surface of a catheter adapter of the IV catheter assembly, holding the spring clip 16 in place until the needle 14 is withdrawn. In response to placement of an IV catheter of the catheter assembly into the vein of the patient, the needle may be retracted or withdrawn proximally. When the needle 14 is withdrawn proximally beyond a distal end of the spring clip 16, the flexible arms may move inwardly, which may first release the interference between the spring clip 16 and the retention feature of the catheter adapter, and then provide a distal barrier for the needle 14, preventing a needle stick injury. Release of the interference between the spring clip 16 and the retention feature may allow removal of the needle assembly 10 from the catheter adapter.

The needle assembly 10 and spring clip 16 may pose several hazards. The spring clip 16 may be constructed of metal and/or may include one or more sharp edges, which may increase a risk that the patient or a clinician may be cut or scratched by the spring clip 16, particularly when the needle assembly 10 is removed from the catheter adapter. In some instances, the sharp edges of the spring clip 16 may be exposed to blood of the patient, and if the clinician contacts the sharp edges, this could lead to infection by one or more blood borne pathogens. Also, the sharp edges of the spring clip 16 may get caught on clothing, bedding, or another material, which may cause the clip to open, allowing a sharp distal tip of the needle to become exposed. Furthermore, an interior lumen of the needle 14 and/or a notch of the needle 14 may be filled with blood, and the blood may spatter or be ejected from the needle 14 when the needle assembly 10 is removed from the catheter adapter.

Figure 2A:
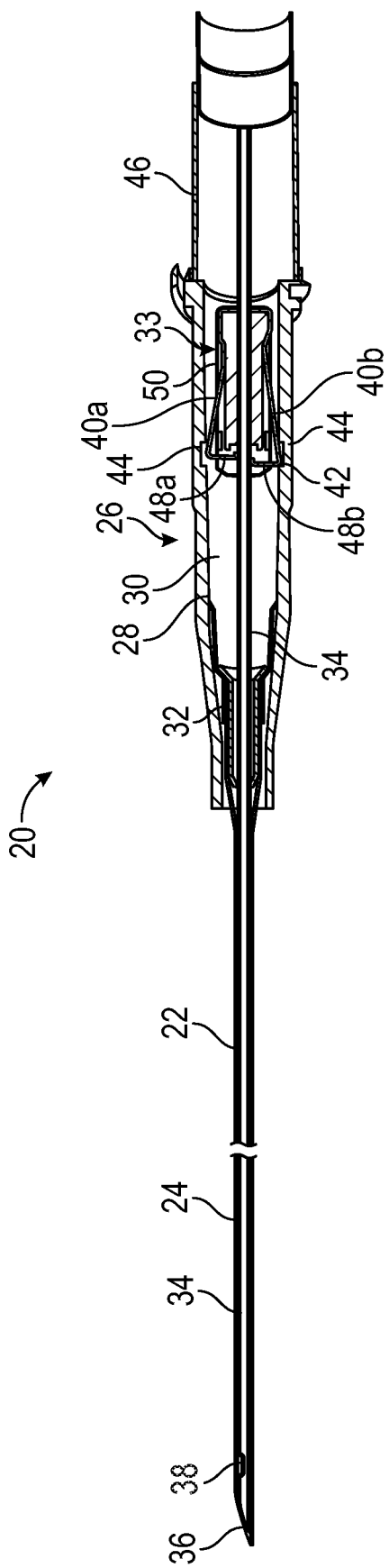
FIG. 2A is a cross-sectional view of an example catheter assembly, illustrating an example needle in a ready position, according to some embodiments.

Referring now to FIGS. 2A-2C, a catheter assembly 20 may overcome disadvantages of the prior art, as will be explained later in further detail. In some embodiments, the catheter assembly 20 may include a catheter 24, which may include a proximal end and a distal end. In some embodiments, the catheter assembly 20 may include a catheter adapter 26, which may include an inner wall 28 forming a lumen 30. In some embodiments, the proximal end of the catheter 24 may be coupled with the catheter adapter 26 via a wedge 32 or another mechanism. In some embodiments, a needle 22 of the catheter assembly 20 may include one or more of the following: an elongated shaft 34, a sharp distal tip 36, a notch 38, and a bump or feature 54. In some embodiments, the notch 38 may improve first stick success and allow observation of blood flashback.

In some embodiments, the needle 22 may be disposed within the catheter 24 when the needle 22 is in a ready position for insertion into the vein of the patient. The ready position is illustrated in FIG. 2A, according to some embodiments. In some embodiments, the needle 22 may be movable between the ready position in which the distal tip 36 is outside of the catheter adapter 26 and a retracted position in which the distal tip 36 is disposed within the lumen 30 of the catheter adapter 26. FIG. 2B illustrates the needle 22 partially withdrawn and between the ready position and the retracted position, according to some embodiments. The retracted position is illustrated in FIG. 2C, according to some embodiments.

In some embodiments, the catheter assembly 20 may include a needle guard 33, which may be unitary or integrally formed. In some embodiments, the needle guard 33 may include a spring clip. In some embodiments, the needle guard 33 may be constructed of a resilient metal, such as, for example, stainless steel. In some embodiments, the needle guard 33 may include one or more resilient arms 40, which may include one or more features for selective coupling of the arms 40 to the inner wall 28 of the catheter adapter 26 or to another component of a catheter device. In some embodiments, the other component may include any suitable component of the catheter device, including, for example, a septum activator, a septum, or a septum canister.

As illustrated in FIGS. 2A-2C, in some embodiments, the needle guard 33 may include first and second resilient arms 40a,b (which may be referred to herein as "resilient arms 40"). In some embodiments, when the needle 22 is in the ready position, the first resilient arm 40a may be entirely disposed on a first side of the needle 22 and the second resilient arm 40b may be entirely disposed on a second side of the needle 22 opposite the first side of the needle 22. In some embodiments, each of the arms 40 may include one or more curved portions 42 or one or more other suitable features for selective coupling of the arms 40 to the other component or to the inner wall 28, such as, for example, one or more protrusions. In some embodiments, the curved portions 42 may each include a bend.

As illustrated in FIGS. 2A-2B, in some embodiments, the curved portions 42 or the other suitable features may be urged by the elongated shaft 34 into retaining contact with the inner wall 28 of the catheter adapter 26 or with the other component when the needle 22 is in the ready position and/or during movement of the needle 22 between the ready position and the retracted position. In some embodiments, the inner wall 28 of the catheter adapter 26 or the other component may include one or more retaining means 44, such as, for example, grooves, bumps, features, or another suitable means that may each receive or interfere with one or more arms 40 in retaining contact. In further detail, in some embodiments, a particular retaining means 44 may receive or interfere with a curved portion 42 of a particular arm 40 and another particular retaining means 44 may receive or interfere with a curved portion 42 of another particular arm 40. In some embodiments, a particular retaining means 44 may receive or interfere with the curved portions of both the particular arms 40. In some embodiments, the retaining means 44 may be annular.

Figure 2D:
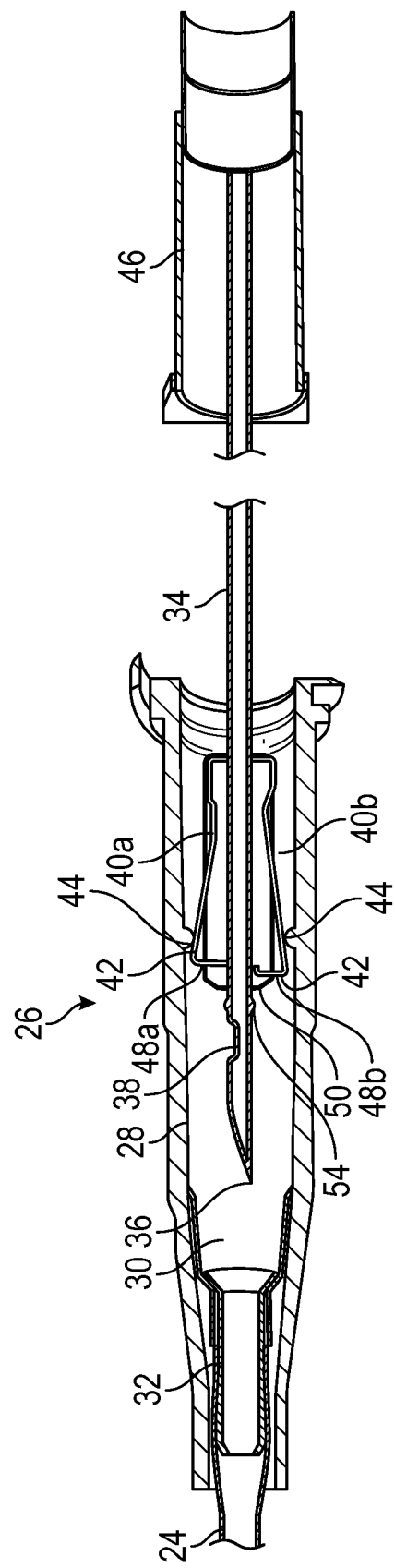
FIG. 2D is a cross-sectional view of the catheter assembly of FIG. 2A, illustrating the needle between the ready position and a retracted position, according to some embodiments.

As illustrated in FIG. 2C, in some embodiments, when the needle 22 is in the retracted position, the elongated shaft 34 may no longer bias or flex the arms 40 outwardly such that the retaining contact between the curved portions 42 and the catheter adapter 26 is released. In some embodiments, a needle assembly 43, which may include one or more of the following: the needle guard 33, the needle 22, a needle hub 46, and a housing 50, may be removed from the catheter adapter 26 in response to the retaining contact between the curved portions 42 and the catheter adapter 26 being released. In some embodiments, the needle hub 46 may include a flash chamber. FIG. 2D illustrates one or more retaining means 44 that each include a bump or protrusion, according to some embodiments.

In some embodiments, the needle guard 33 may include one or more distal walls 48, which may form a distal barrier to the needle 22 when the needle 22 is in the retracted position. In some embodiments, the distal walls 48 may contact and/or overlap one another. For example, the needle guard 33 may include first and second distal walls 48a,b that contact and overlap each other, as illustrated in FIG. 2C.

Figure 3A:
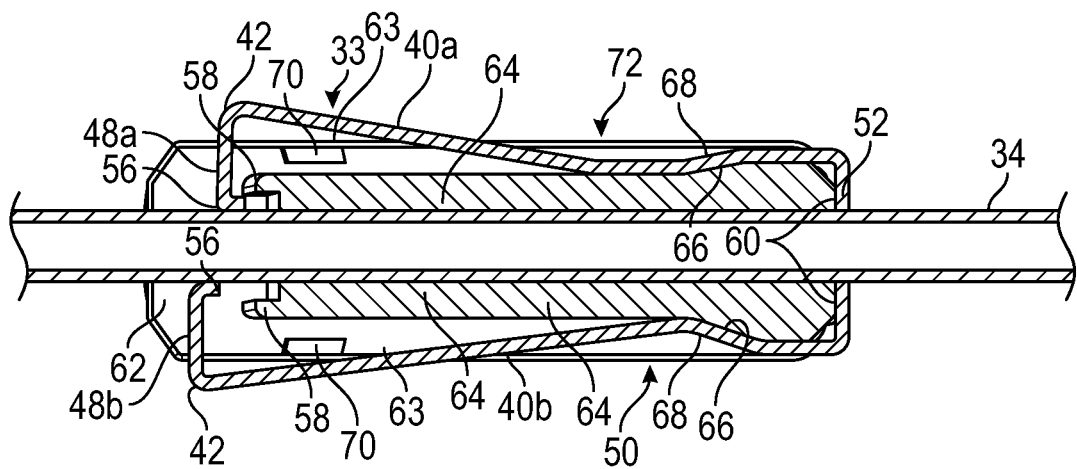
FIG. 3A is a cross-sectional view of an example needle assembly of the catheter assembly of FIG. 2A, illustrating the needle in the ready position, according to some embodiments.
Figure 3B:
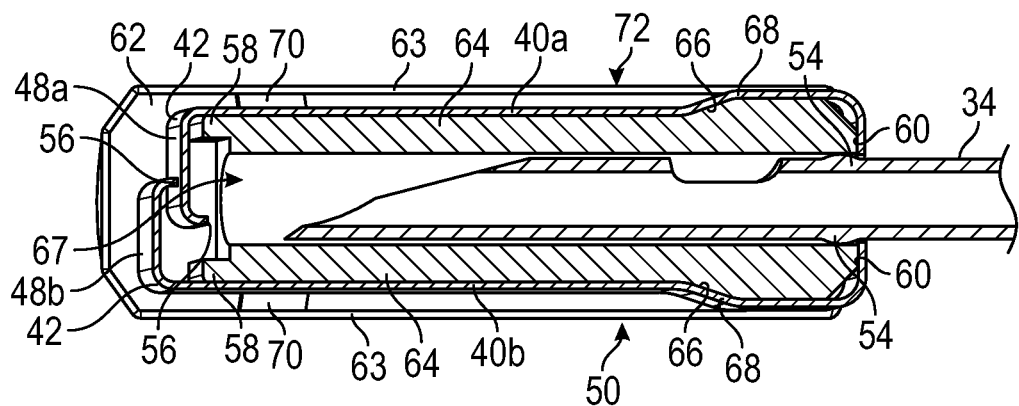
FIG. 3B is a cross-sectional view of the needle assembly of FIG. 3A, illustrating the needle in a retracted position, according to some embodiments.

Referring now to FIGS. 3A-3B, in some embodiments, a particular distal wall 48 may extend from and be continuous with a particular arm 40, which may extend between the particular distal wall 48 and a proximal end wall 52 of the needle guard 33. In some embodiments, the proximal end wall 52 may include an opening for receiving the needle 22 there through. In some embodiments, the elongated shaft 34 of the needle 22 may include a feature 54, which may have a diameter larger than a diameter of the opening in the proximal end wall 52, preventing the distal tip 36 from exiting proximally through the opening in the proximal end wall 52.

In some embodiments, one or more of the distal walls 48 may include a lip 56, which may engage the elongated shaft 34 of the needle 22 when the needle 22 is in the ready position, as illustrated in FIG. 3A. In some embodiments, each of the distal walls 48 may be movable within the lumen 30 of the catheter adapter 26 to blocking positions distal of the distal tip 36, as illustrated in FIG. 3B. In some embodiments, each of the distal walls 48 may be in their respective blocking positions when the needle 22 is in the retracted position. In some embodiments, the distal walls 48 may contact and/or overlap one another to form a distal barrier to the needle 22 when the distal walls 48 are in their respective blocking positions.

In some embodiments, the housing 50 may cover any sharp edges of the needle guard 33, preventing contact with the sharp edges. For example, when the needle 33 is in the retracted position, at least edges of the arms 40, the distal walls 48, and the proximal end wall 52 may be disposed within an outer edge or perimeter of the housing 50. In some embodiments, the housing 50 and the needle guard 33 may together enclose the distal tip 36 when the needle 22 is in the retracted position, which may prevent exposure to the distal tip 36 and any blood that may be released from the distal tip 36 and/or the notch 38. In some embodiments, the housing 50 may be unitary or integrally formed.

In some embodiments, an inner surface 62 of the housing 50 may include one or more distal features 58 and/or one or more proximal features 60, which may prevent separation of the housing 50 from the needle guard 33. In some embodiments, each of the distal features 58 may be configured to contact a proximal surface of a particular distal wall 48 of the needle guard 33 to prevent the needle guard 33 from sliding proximally with respect to the housing 50. In some embodiments, each of the proximal features 60 may be configured to contact a distal surface of the proximal end wall 52 to prevent the needle guard 33 from sliding distally with respect to the housing 50.

In some embodiments, the distal features 58 and/or the proximal features 60 may include protrusions, which may extend inwardly from the inner surface 62 of the housing 50. In some embodiments, the inner surface 62 may include a tubular structure, which may include a wall 64 forming a lumen 30 extending through the tubular structure. In some embodiments, the needle 33 may extend through the lumen 30 of the tubular structure. In some embodiments, the distal features 58 and/or the proximal features 60 may extend from the wall 64 and/or be unitary or integrally formed with the wall 64, which may be unitary or integrally formed with the inner surface 62. In some embodiments, the distal walls 48 may cover a distal opening 67 of the tubular structure such that the distal walls 48 and the housing 50 enclose the distal tip 36 and/or the notch 38.

In some embodiments, an outer surface of the wall 64 may include an angled portion 66, which may correspond to an angled portion 68 of a particular arm 40. In some embodiments, the angled portion 66 may inhibit proximal movement of the needle guard 33 with respect to the housing 50. In some embodiments, the housing 50 may include one or more snap features 70 configured to secure the needle guard 33 within the housing 50 when the needle 33 is in the retracted position. In some embodiments, the inner surfaces 62 and/or inner edges 63 of the shield elements 72 may include the snap features 70. In some embodiments, opposing snap features 70 disposed on opposing shield elements 72 may contact an outer surface of a particular arm 40 when the needle 33 is in the retracted position.

Figure 4A:
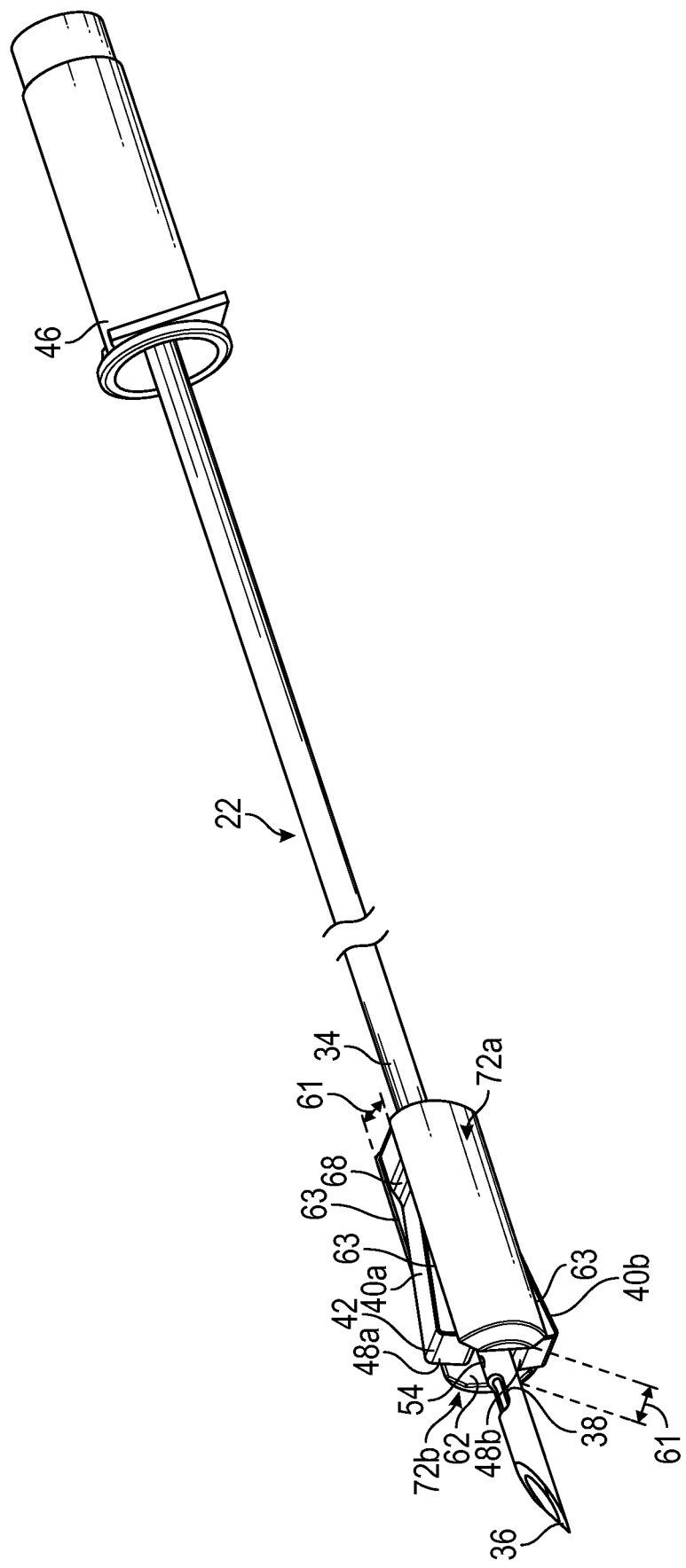
FIG. 4A is an upper perspective view of the needle assembly of FIG. 3A, illustrating the needle between the ready position and the retracted position, according to some embodiments.
Figure 4B:
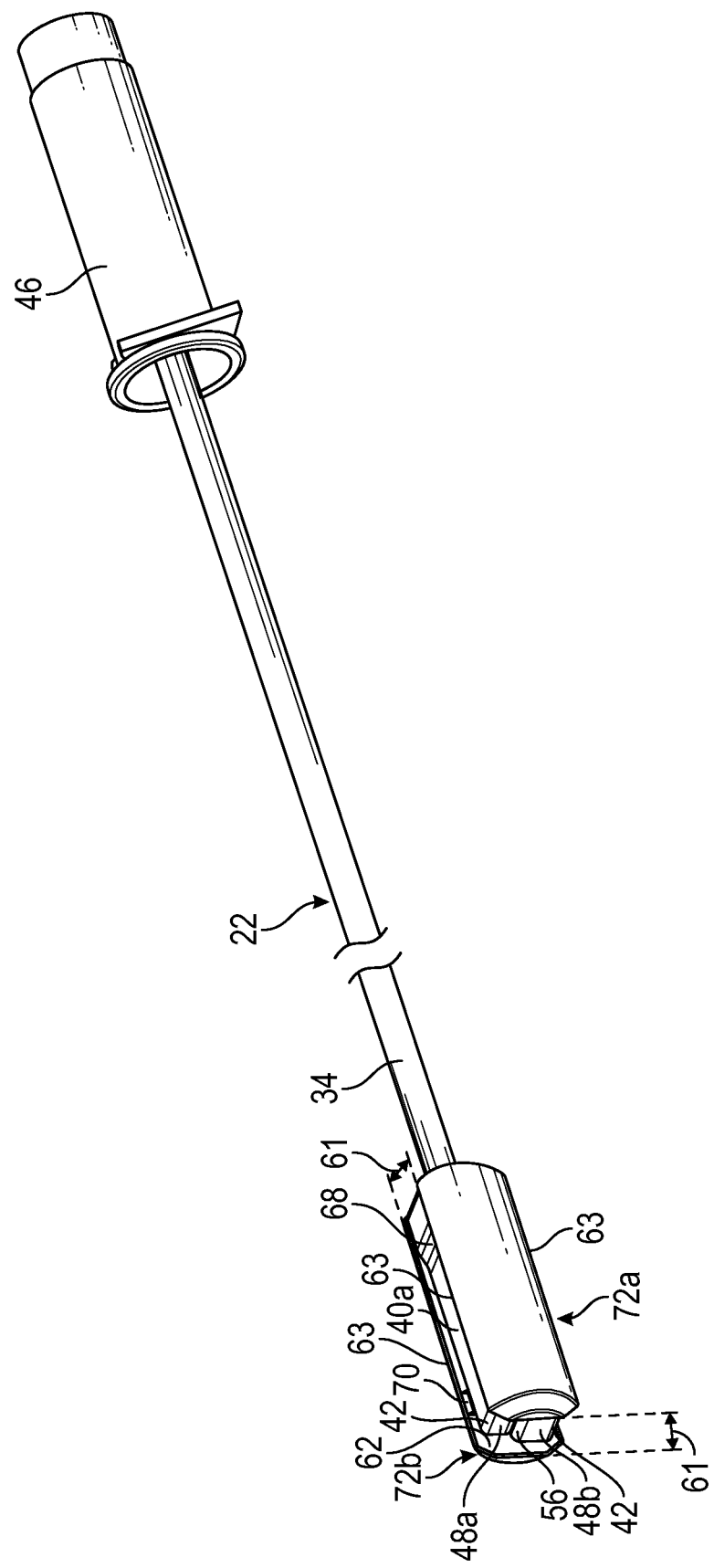
FIG. 4B is an upper perspective view of the needle assembly of FIG. 3A, illustrating the needle in a retracted position, according to some embodiments.

In some embodiments, the housing 50 may include multiple elongated shield elements 72, which may shield a user from one or more edges of the needle guard 33 that may otherwise scratch or cut the user. Referring now to FIGS. 4A-4B, for example, the housing may include a first shield element 72a and a second shield element 72b (which may referred to in the present disclosure as "shield elements 72"), which may be disposed opposite of each other. In some embodiments, the shield elements 72 may be spaced apart. In some embodiments, the shield elements 72 may be spaced apart by a gap 61 between inner edges 63 of the shield elements 72. In some embodiments, the arms 40 may be urged outwardly by the elongated shaft 34 through the gap 61 when the needle 33 is in the ready position and/or in between the ready position and the retracted position, as illustrated in FIG. 4A. In some embodiments, one or more of the following may extend between inner surfaces of the shield elements 72: the distal features 58, the proximal features 60, and the tubular structure. In some embodiments, the inner surface 62 of the housing 50 may correspond to an inner surface of one or more particular shield elements 72.

Referring now to FIGS. 5A-5B, in some embodiments, the first shield element 72a may be connected to the second shield element 72b at a joiner wall 74, which may cover all or a portion of the proximal end wall 52. In some embodiments, the needle 33 may extend through a hole in the joiner wall 74.

Figure 5C:
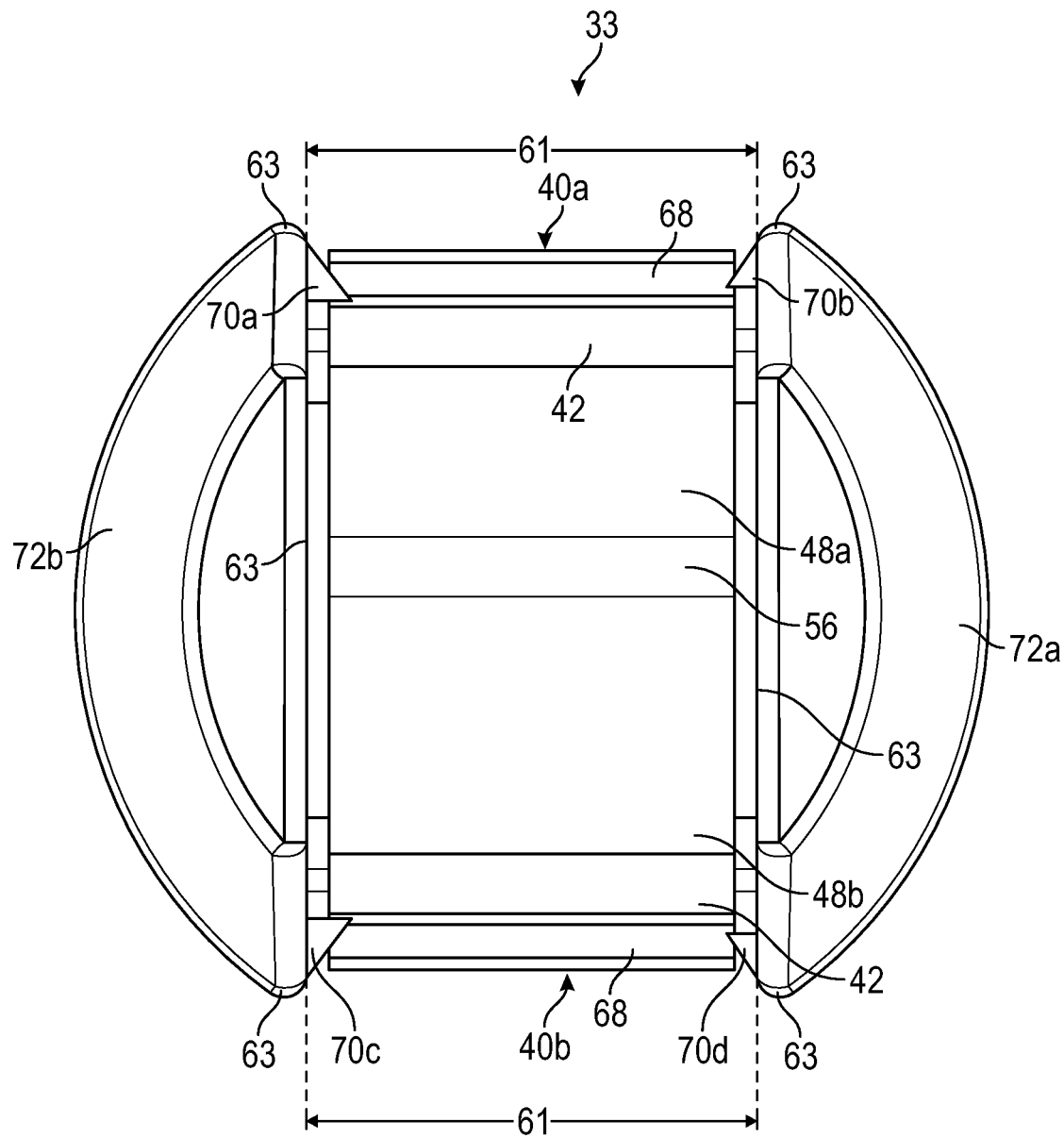
FIG. 5C is a distal view of the needle assembly of FIG. 3A, illustrating the needle in the retracted position, according to some embodiments.

Referring now to FIG. 5C, in some embodiments, the arms 40 may snap past the snap features 70 in response to the needle 33 moving from the ready position to the retracted position. In further detail, in some embodiments, the snap features 70 may be resilient and may easily deform to allow the arms 40 to pass, thereafter resuming their original conformation.

The snap features 70 may have various locations and sizes that facilitate rocking or tilting of the resilient arms 40 and movement of the resilient arms 40 to a locked position beneath the snap features 70 and towards a central axis of the housing 50 and/or the needle guard 33. In some embodiments, a first snap feature 70a and a second snap feature 70b may be disposed on opposite sides of the housing 50. In some embodiments, the first snap feature 70a may be aligned with or oppose the second snap feature 70b, as illustrated in FIG. 5C. In some embodiments, the first snap feature 70a and second snap feature 70b may be not be aligned with or oppose each other. In some embodiments, the first snap feature 70a and the second snap feature 70b may be a same or similar shape but different sizes. In these and other embodiments, the first snap feature 70a may extend more inwardly than the second snap feature 70b, as illustrated in FIG. 5C, such that a particular resilient arm 40 may pass the second snap feature 70b before the first snap feature 70a when the needle moves from the ready position to the retracted position, which may result in rocking or tilting the particular resilient arm 40 and facilitating movement of the particular resilient arm 40 to a locked position beneath the first snap feature 70a and second snap feature 70b. In some embodiments, the particular resilient arm 40 may contact the first snap feature 70a prior to the second snap feature 70b, which may also result in the rocking or tilting of the particular resilient arm 40.

In some embodiments, the housing 50 may include one or more additional snap features 70. In some embodiments, the housing 50 may include third and fourth snap features 70c, 70d, which may be positioned and/or sized with respect to each other similarly to first snap feature 70a and second snap feature 70b.

Figure 6A:
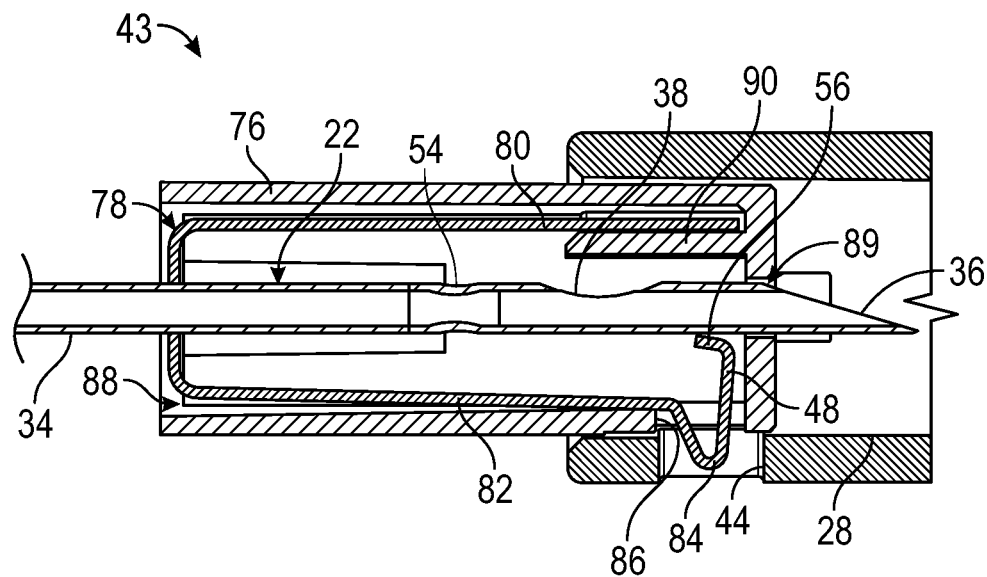
FIG. 6A is a cross-sectional view of another example needle assembly, illustrating the needle in a partially retracted position, according to some embodiments.
Figure 6B:
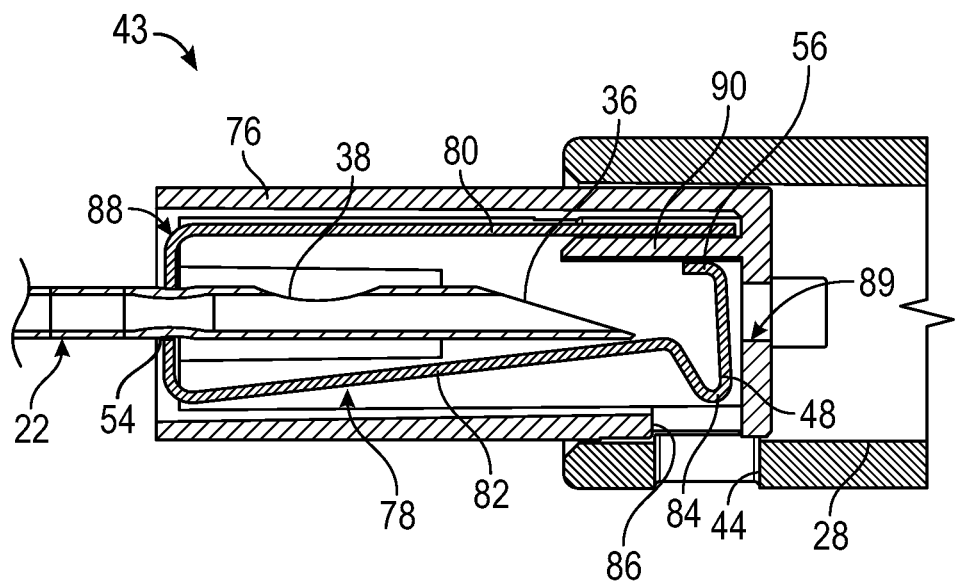
FIG. 6B is a cross-sectional view of the needle assembly of FIG. 6A, illustrating the needle in the retracted position, according to some embodiments.

Referring now to FIG. 6A-6B, in some embodiments, the needle assembly 43 may include a housing 76 and/or a needle guard 78. In some embodiments, the needle guard 78 may be unitary or integrally formed. In some embodiments, the needle guard 78 may include a spring clip. In some embodiments, the needle guard 78 may be constructed of a resilient metal, such as, for example, stainless steel.

In some embodiments, the needle guard 78 may include an upper arm 80 and a lower arm 82. In some embodiments, the lower arm 82 may include a curved portion 84 or one or more other suitable features, such as, for example, one or more protrusions, for selective coupling of the lower arm 82 to the inner wall 28 of the catheter adapter 26 or to another component of a catheter device. In some embodiments, the other component may include any suitable component of the catheter device, including, for example, a septum activator, a septum, or a septum canister.

In some embodiments, the upper arm 80 may be coupled to the housing 76. In some embodiments, the upper arm 80 may be coupled to the housing 76 along all or a portion of a length of the upper arm 80. In some embodiments, the upper arm 80 may be permanently coupled to the housing 76.

In some embodiments, when the needle 22 is in the ready position or partially retracted position, as illustrated in FIG. 6A, the curved portion 84 or the other suitable features may be urged by the needle 22 into retaining contact with the inner wall 28 of the catheter adapter 26 or with the other component. In these and other embodiments, the curved portion 84 may extend through a distal aperture 86 in the housing 76 of the needle assembly 43, the distal aperture 86 being aligned with the retaining means 44 of the inner wall 28 of the catheter adapter 26. The retaining means 44 may include a groove or aperture or another suitable means that may each receive or interfere with the lower arm 82 in retaining contact. In further detail, in some embodiments, a particular retaining means 44 may receive or interfere with the curved portion 84.

In some embodiments, when the needle 22 is retracted, the needle 22 may no longer bias the lower arm 82 outwardly such that the retaining contact between the lower arm 82 and the catheter adapter 26 is released and the lower arm 82 resiliently moves inwardly. In these embodiments, the housing 76 and the needle guard 78 may be removable from the catheter adapter 26.

In some embodiments, the distal wall 48 may include a lip 56, which may engage the needle 22 when the needle 22 is in the ready position and/or the partially retracted position, as illustrated in FIG. 6A. In some embodiments, the lower arm 82 may include a distal wall 48, which may form a distal barrier to the needle 22 when the needle 22 is in the retracted position, as illustrated in FIG. 6B. In some embodiments, the distal wall 48 of the lower arm 82 may prevent the needle 22 from exiting a distal opening 89 in the distal end of the housing 76, when the needle 22 is in the retracted position.

In some embodiments, when the needle 22 is in the retracted position, the distal wall 48 and/or the lip 56 may contact a shelf 90 of the housing 76. In some embodiments, the shelf 90 may support the lower arm 82 and/or separate at least a portion of the upper arm 80 from the lower arm 82. In some embodiments, the shelf 90 may extend from a distal end and/or side of the housing 76.

In some embodiments, the proximal end of the housing 76 may include a proximal opening 88 for receiving the needle 22 and/or the needle guard 78 there through. In some embodiments, the elongated shaft 34 of the needle 22 may include a feature 54, which may prevent the distal tip 36 from exiting proximally through a proximal opening in a proximal end wall 52 of the needle guard 78.

In some embodiments, the housing 76 may cover any sharp edges of the needle guard 33, preventing contact with the sharp edges. For example, when the needle 22 is in the retracted position, at least edges of the lower arm 82, upper arm 80, the distal wall 48, and the proximal end wall 52 may be disposed within an outer edge or perimeter of the housing 76. In some embodiments, when the needle 22 is in the retracted position, an entirety of the needle guard 78 may be disposed within the outer edge or perimeter of the housing 76. In some embodiments, the housing 76 and the needle guard 78 may together enclose the distal tip 36 when the needle 22 is in the retracted position, which may prevent exposure to the distal tip 36 and any blood that may be released from the distal tip 36 and/or the notch 38. In some embodiments, the housing 76 may be unitary or integrally formed.

Figure 6C:
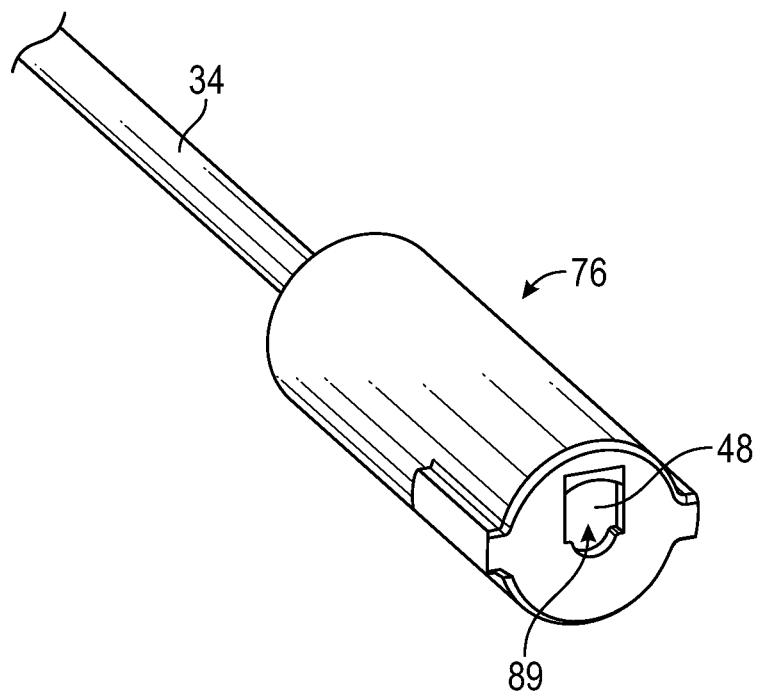
FIG. 6C is an upper perspective view of the needle assembly of FIG. 6A, illustrating the needle in the retracted position, according to some embodiments.
Figure 6D:
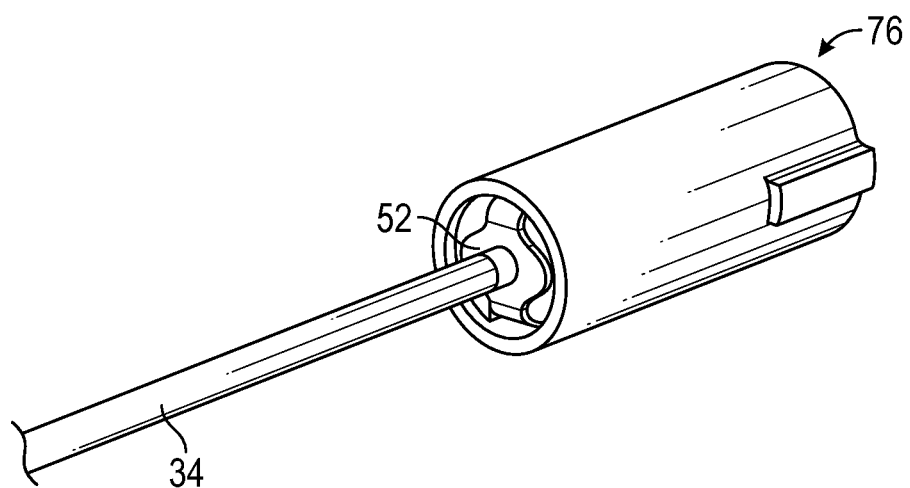
FIG. 6D is an upper perspective view of the needle assembly of FIG. 6A, illustrating the needle in the retracted position, according to some embodiments.

Referring now to FIG. 6C, in some embodiments, the housing 76 may be generally tubular. Referring now to FIG. 6D, in some embodiments, the proximal opening 88 may be blocked by the proximal end wall 52 of the needle guard 78 that connects the upper arm 80 and the lower arm 82. In some embodiments, the housing 76 may be continuous apart from one or more of the following: the distal opening 89, the distal aperture 86, and the proximal opening 88.

Figure 6E:
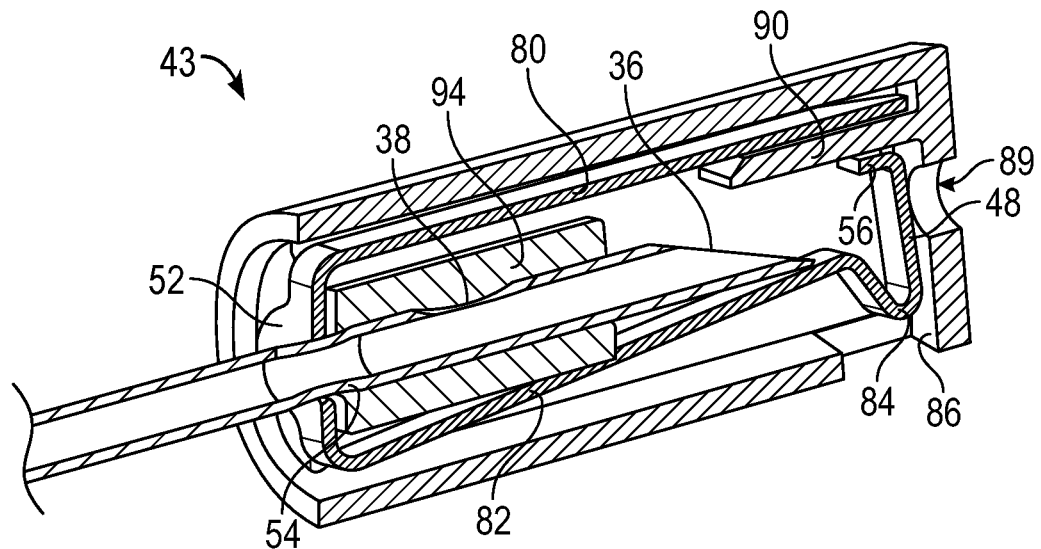
FIG. 6E is a cross-sectional view of the needle assembly of FIG. 6A, illustrating an example stabilizer element, according to some embodiments.

Referring now to FIG. 6E, in some embodiments, the needle assembly 43 may include a stabilizer element 94, which may be integrally formed with the housing 76. In some embodiments, the stabilizer element 94 may be disposed within the needle guard 78 and/or may include a channel through which the needle 22 may extend.

Figure 6F:
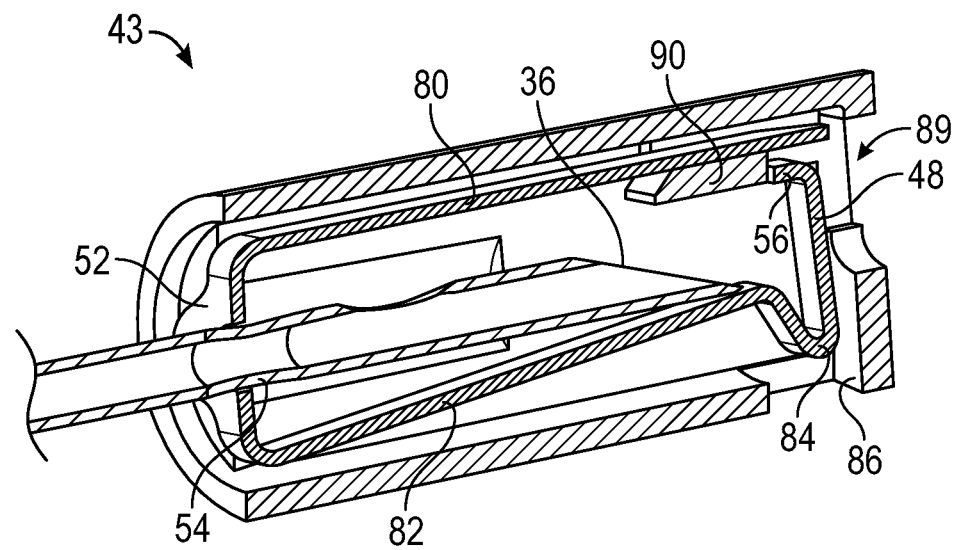
FIG. 6F is a cross-sectional view of the needle assembly of FIG. 6A, illustrating an example platform, according to some embodiments.

Referring now to FIG. 6F, in some embodiments, the distal wall 48 and/or the lip 56 may be configured to contact a distal end of the shelf 90. In some embodiments, when the needle 22 is in the retracted position, as illustrated in FIG. 6F, the distal wall 48 and/or the lip 56 may be disposed distal to the distal end of the shelf 90 and above an inner surface of the shelf 90. In these and other embodiments, the distal wall 48 and/or the lip 56 may contact the distal end of the shelf 90. In these and other embodiments, the distal tip 36 of the needle 22 may not be coerced to contact the lip or an edge of the lip 56 in contact with the distal end of the shelf 90, which may increase a robustness of the needle assembly 43 in preventing needle stick injury. In some embodiments, the distal end of the shelf 90 may act as a stop to prevent the needle guard 78 from exiting the proximal opening 88 of the housing 76 and/or sliding proximally with respect to the housing 76.

The present invention may be embodied in other specific forms without departing from its structures, methods, or other essential characteristics as broadly described herein and claimed hereinafter. For example, it is understood that the housing 50 may have various configurations and shapes designed to cover one or more sharp edges of the needle guard 33 and/or enclose the distal tip 36 and/or the notch 38. The described embodiments and examples are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed is:

1. An intravenous catheter assembly, comprising:
   a catheter comprising a proximal end and a distal end;
   a catheter adapter comprising an inner wall forming a lumen, wherein the proximal end of the catheter is coupled with the catheter adapter;
   a needle comprising an elongated shaft and distal tip, wherein the needle is disposed within the catheter when the needle is in a ready position, wherein the needle is movable between the ready position in which the distal tip is outside of the catheter adapter and a retracted position in which the distal tip is disposed within the lumen of the catheter adapter;
   a needle guard, comprising:
      first and second distal walls that overlap one another and form a distal barrier to the needle when the needle is in the retracted position;
      a proximal end wall comprising an opening for receiving the needle therethrough; and
      first and second resilient arms comprising first and second curved portions, respectively, wherein the first and second resilient arms extend between the first and second distal walls, respectively, and the proximal end wall, wherein the first and second curved portions contact the inner wall of the catheter adapter when the needle is in the ready position and during movement of the needle between the ready position and the retracted position, wherein when the needle is in the retracted position, the elongated shaft no longer biases the first and second resilient arms outwardly such that the first and second curved portions do not contact the catheter adapter and the catheter adapter is released; and
   a housing coupled to the needle guard such that the needle guard is disposed within the housing and wherein the housing and the needle guard enclose the distal tip when the needle is in the retracted position, wherein the housing is disposed within the lumen, wherein the housing comprises a first shield element and a second shield element opposite the first shield element, wherein the first and second shield elements are spaced apart by a gap, wherein the housing comprises an elongated tubular structure disposed between the first resilient arm and the second resilient arm, where the needle extends through the elongated tubular structure, wherein an outer surface of the tubular structure comprises an angled portion corresponding and adjacent to an angled portion of the first resilient arm or the second resilient arm, wherein the angled portion of the outer surface and the angled portion of the first resilient arm or the second resilient arm inhibit proximal movement of the needle guard with respect to the housing.

2. The intravenous catheter assembly of claim 1, wherein the needle further comprises a notch, wherein the housing and the needle guard enclose the distal tip and the notch when the needle is in the retracted position.

3. The intravenous catheter assembly of claim 1, wherein the gap extends generally linearly along a longitudinal axis of the needle, wherein the first and second resilient arms are urged outwardly by the elongated shaft and extend through the gap when the needle is in the ready position.

4. The intravenous catheter assembly of claim 3, wherein the first resilient arm and the second resilient arm contact the angled portion and a portion of the elongated tubular structure between a distal end of the tubular portion and the angled portion in response to the needle being moved to the retracted position.

5. The intravenous catheter assembly of claim 1, wherein an inner surface of the housing comprises a distal surface and a proximal surface, wherein the distal surface is configured to contact a proximal surface of the first distal wall to prevent the needle guard from sliding proximally with respect to the housing, wherein the proximal surface of the inner surface of the housing is configured to contact a distal surface of the proximal end wall to prevent the needle guard from sliding distally with respect to the housing.

6. The intravenous catheter assembly of claim 1, wherein the housing and the needle guard are removable from the catheter adapter when the needle is in the retracted position.

7. The intravenous catheter assembly of claim 3, wherein an inner edge of the first shield element comprises a protrusion that extends into the gap, wherein the protrusion contacts an outer surface of the first resilient arm when the needle is in the retracted position.

8. The intravenous catheter assembly of claim 7, wherein the protrusion is a first protrusion, wherein an inner edge of the second shield element comprises a second protrusion that extends into the gap, wherein the first resilient arm passes the second protrusion before the first resilient arm passes the first protrusion when the needle moves from the ready position to the retracted position.

9. The intravenous catheter assembly of claim 1, wherein the first distal wall and the second distal wall comprise first and second lips, respectively, wherein the first and second lips engage the elongated shaft of the needle when the needle is in the ready position.

10. The intravenous catheter assembly of claim 1, wherein when the needle is in the ready position, the first resilient arm is entirely disposed on a first side of the needle and the second resilient arm is entirely disposed on a second side of the needle opposite the first side of the needle.

11. The intravenous catheter assembly of claim 1, wherein the inner wall of the catheter adapter comprises a groove, a protrusion, or an aperture, wherein the groove, the protrusion, or the aperture receives the first curved portion of the first resilient arm when the needle is in the ready position.

12. An intravenous catheter assembly, comprising:
a catheter comprising a proximal end and a distal end;
a catheter adapter comprising an inner wall forming a lumen, wherein the proximal end of the catheter is coupled with the catheter adapter;
a needle comprising an elongated shaft and distal tip, wherein the needle is disposed within the catheter when the needle is in a ready position, wherein the needle is movable between the ready position in which the distal tip is outside of the catheter adapter and a retracted position in which the distal tip is disposed within the lumen of the catheter adapter;
a needle guard, comprising:
first and second distal walls that overlap one another and form a distal barrier to the needle when the needle is in the retracted position;
a proximal end wall comprising an opening for receiving the needle therethrough;
first and second resilient arms comprising first and second curved portions, respectively, wherein the first and second resilient arms extend between the first and second distal walls, respectively, and the proximal end wall, wherein the first and second curved portions contact the inner wall of the catheter adapter when the needle is in the ready position and during movement of the needle between the ready position and the retracted position, wherein when the needle is in the retracted position, the elongated shaft no longer biases the first and second resilient arms outwardly such that the first and second curved portions do not contact the catheter adapter and the catheter adapter is released; and
a housing disposed within the lumen and coupled to the needle guard such that each of the first distal wall and the second distal wall is disposed within the housing when the needle is in the ready position and the first and second distal walls enclose the distal tip within the housing when the needle is in the retracted position.

13. The intravenous catheter assembly of claim 12, wherein the needle further comprises a notch, wherein the housing and the needle guard enclose the distal tip and the notch when the needle is in the retracted position.

14. The intravenous catheter assembly of claim 12, wherein the housing comprises a first shield element and a second shield element opposite the first shield element, wherein the first and second shield elements are spaced apart by a gap, wherein the gap extends generally linearly along a longitudinal axis of the needle, wherein the first resilient arm and the second resilient arm are urged outwardly by the elongated shaft and extend through the gap when the needle is in the ready position.

15. The intravenous catheter assembly of claim 12, wherein an inner surface of the housing comprises a distal surface and a proximal surface, wherein the distal surface is configured to contact a proximal surface of the first distal wall to prevent the needle guard from sliding proximally with respect to the housing, wherein the proximal surface of the inner surface of the housing is configured to contact a distal surface of the proximal end wall to prevent the needle guard from sliding distally with respect to the housing.

16. The intravenous catheter assembly of claim 14, wherein an inner edge of the first shield element comprises a first protrusion that extends into the gap and an inner edge of the second shield element comprises a second protrusion that extends into the gap, wherein when the needle is in the retracted position, the first protrusion contacts an outer surface of the first resilient arm.

17. The intravenous catheter assembly of claim 16, wherein the first resilient arm passes the second protrusion before the first resilient arm passes the first protrusion when the needle moves from the ready position to the retracted position.

18. The intravenous catheter assembly of claim 1, wherein the first distal wall or the second distal wall comprises a lip, wherein the lip engages the elongated shaft of the needle when the needle is in the ready position.

19. The intravenous catheter assembly of claim 12, wherein the inner wall of the catheter adapter comprises a groove, a protrusion, or an aperture, wherein the groove, the protrusion, or the aperture receives the first resilient arm or the second resilient arm when the needle is in the ready position.

20. The intravenous catheter assembly of claim 1, wherein in response to the needle being in the retracted position, a portion of the first resilient arm extending from the first curved portion to the angled portion is generally parallel to a portion of the second resilient arm extending from the second curved portion to the angled portion.

* * * * *